US009727139B2

(12) United States Patent
Ramsay et al.

(10) Patent No.: US 9,727,139 B2
(45) Date of Patent: Aug. 8, 2017

(54) METHOD AND APPARATUS FOR PROVIDING A HAPTIC MONITORING SYSTEM USING MULTIPLE SENSORS

(75) Inventors: Erin B. Ramsay, Montreal (CA); Robert W. Heubel, San Leandro, CA (US); Neil Olien, Montreal (CA)

(73) Assignee: Immersion Corporation, San Jose, CA (US)

( * ) Notice: Subject to any disclaimer, the term of this patent is extended or adjusted under 35 U.S.C. 154(b) by 752 days.

(21) Appl. No.: 12/334,330

(22) Filed: Dec. 12, 2008

(65) Prior Publication Data

US 2010/0152545 A1    Jun. 17, 2010

(51) Int. Cl.
*G06F 3/00* (2006.01)
*A61B 5/00* (2006.01)
(Continued)

(52) U.S. Cl.
CPC ............ *G06F 3/016* (2013.01); *A61B 5/0002* (2013.01); *A61B 5/02055* (2013.01);
(Continued)

(58) Field of Classification Search
CPC .... A61B 5/150809; A61B 2018/00297; A61B 5/02; G06F 3/011–3/016; G06F 2203/13; G06F 2203/014; G06F 19/3406; G08B 6/00
USPC ........ 600/300–301, 307, 363–365, 372–384, 600/386–394, 412, 481, 483, 484, 485, 600/500–503, 508, 515–519, 529–534, 600/544–547, 549, 587–595; 128/920–925; 705/2–3
See application file for complete search history.

(56) References Cited

U.S. PATENT DOCUMENTS 5,395,301 A * 3/1995 Russek ........................ 601/41
5,555,891 A * 9/1996 Eisenfeld ............ A61B 5/0809
600/534
(Continued)

FOREIGN PATENT DOCUMENTS

CN        101057795     10/2007
JP        2005-095570   4/2005
(Continued)

OTHER PUBLICATIONS

International Search Report and Written Opinion—PCT/US2009/066910, dated Mar. 11, 2010.
(Continued)

*Primary Examiner* — Mary Zeman
*Assistant Examiner* — Marie Archer
(74) *Attorney, Agent, or Firm* — Miles & Stockbridge P.C.

(57) ABSTRACT

A method and apparatus providing a haptic monitor system capable of generating haptic cues based on sensed information are disclosed. The haptic system includes a sensing device, a digital processing unit, and a haptic generator. The sensing device is configured to selectively sense an individual's or user vital information via one or more wearable sensors, and subsequently forwards the sensed vital information to the digital processing unit for data processing. Upon receipt of the vital information, the digital processing unit provides a haptic signal in response to the vital information. The haptic generator, subsequently, generates haptic feedback in accordance with the haptic signal.

24 Claims, 9 Drawing Sheets

(51) Int. Cl.
*G06F 19/00* (2011.01)
*G06F 3/01* (2006.01)
*A61B 5/0205* (2006.01)
*A61B 5/021* (2006.01)
*A61B 5/024* (2006.01)
*A61B 5/08* (2006.01)
*A61B 5/11* (2006.01)

(52) U.S. Cl.
CPC ............ *A61B 5/7455* (2013.01); *G06F 3/011* (2013.01); *G06F 19/3418* (2013.01); *A61B 5/021* (2013.01); *A61B 5/02438* (2013.01); *A61B 5/0816* (2013.01); *A61B 5/1112* (2013.01); *A61B 5/681* (2013.01); *G06F 2203/011* (2013.01)

(56) References Cited

U.S. PATENT DOCUMENTS

| | | | |
|---|---|---|---|
| 6,147,674 A | 11/2000 | Rosenberg et al. | |
| 6,198,394 B1 | 3/2001 | Jacobsen et al. | |
| 6,398,728 B1 | 6/2002 | Bardy | |
| 6,563,487 B2 | 5/2003 | Martin et al. | |
| 6,695,770 B1 | 2/2004 | Choy et al. | |
| 6,790,178 B1 | 9/2004 | Mault et al. | |
| 7,039,866 B1 | 5/2006 | Rosenberg et al. | |
| 7,046,151 B2 | 5/2006 | Dundon | |
| 7,082,570 B1* | 7/2006 | von Wiegand et al. | 715/702 |
| 7,159,008 B1 | 1/2007 | Wies et al. | |
| 7,510,398 B1* | 3/2009 | Thornton | G09B 23/288 434/262 |
| 8,092,355 B2 | 1/2012 | Mortimer et al. | |
| 8,226,479 B2* | 7/2012 | Crawford et al. | 463/36 |
| 8,228,202 B2 | 7/2012 | Buchner et al. | |
| 8,651,964 B2 | 2/2014 | Brick | |
| 2001/0045935 A1* | 11/2001 | Chang | G05B 19/00 345/156 |
| 2004/0078219 A1 | 4/2004 | Kaylor et al. | |
| 2004/0090318 A1 | 5/2004 | Rothkop | |
| 2005/0097970 A1 | 5/2005 | Nurse | |
| 2005/0113167 A1* | 5/2005 | Buchner et al. | 463/30 |
| 2005/0113703 A1 | 5/2005 | Farringdon et al. | |
| 2006/0010090 A1 | 1/2006 | Brockway et al. | |
| 2006/0015560 A1* | 1/2006 | MacAuley et al. | 709/206 |
| 2006/0038781 A1* | 2/2006 | Levin | 345/163 |
| 2006/0063980 A1 | 3/2006 | Hwang et al. | |
| 2006/0105838 A1* | 5/2006 | Mullen | 463/31 |
| 2007/0038038 A1* | 2/2007 | Stivoric et al. | 600/300 |
| 2007/0038164 A1* | 2/2007 | Afshar | 601/47 |
| 2007/0063850 A1* | 3/2007 | Devaul et al. | 340/573.1 |
| 2008/0025323 A1* | 1/2008 | Khan | 370/400 |
| 2008/0146892 A1* | 6/2008 | LeBoeuf | A61B 5/11 600/300 |
| 2008/0214903 A1* | 9/2008 | Orbach | 600/301 |
| 2008/0274769 A1 | 11/2008 | Linden | |
| 2009/0048070 A1 | 2/2009 | Vincent et al. | |
| 2009/0062092 A1 | 3/2009 | Mortimer et al. | |
| 2009/0062686 A1* | 3/2009 | Hyde et al. | 600/558 |
| 2009/0076723 A1* | 3/2009 | Moloney | 701/209 |
| 2009/0085873 A1 | 4/2009 | Betts et al. | |
| 2009/0128306 A1* | 5/2009 | Luden et al. | 340/407.1 |
| 2009/0131165 A1 | 5/2009 | Buchner et al. | |
| 2009/0221890 A1 | 9/2009 | Saffer et al. | |
| 2009/0253109 A1 | 10/2009 | Anvari et al. | |
| 2010/0027378 A1* | 2/2010 | Sabatier | G08B 13/1672 367/136 |
| 2010/0033303 A1* | 2/2010 | Dugan et al. | 340/5.82 |
| 2010/0079264 A1* | 4/2010 | Hoellwarth | 340/407.2 |
| 2010/0152620 A1 | 6/2010 | Ramsay et al. | |
| 2011/0009711 A1* | 1/2011 | Nanikashvili et al. | 600/301 |
| 2011/0121965 A1 | 5/2011 | Betts et al. | |

FOREIGN PATENT DOCUMENTS

| | | |
|---|---|---|
| JP | 2008-524589 A | 7/2008 |
| WO | WO 01/00281 A2 | 1/2001 |
| WO | WO 2007/070155 | 6/2007 |

OTHER PUBLICATIONS

"Clothing gives sportsmen a kick up the pants," Internet Citation, Sep. 29, 2005, XP007912027, Retrieved from the Internet: URL:http://www.we-make-money-not-art.com/archives/2005/09/as-if-being-baw.ph, retrieved on Mar. 2, 2010.

Van Erp, J. et al., "Waypoint Navigation with a Vibrotactile Waist Belt," ACM Transactions on Applied Perception, Association for Computing Machinery, Inc., New York, NY, US, vol. 2., No. 2, Apr. 1, 2005, pp. 106-117, XP002408374, ISSN: 1544-3558, paragraph [0001]—paragraph [0004].

Notification of Reasons for Refusal as issued for Japanese Patent Application No. 2011-540792, dated Jan. 7, 2014.

Office Action issued for Chinese Patent Application No. 200980149457.6, dated Apr. 18, 2014.

Notification of Reason for Refusal issued in Japanese Patent Application No. JP 2011-540792, dated Oct. 2, 2014.

Notification of Third Office Action issued in Chinese Patent Application No. CN 200980149457.6, dated Oct. 20, 2014.

Examination Report issued in European Patent Application No. 09 802 061.3, dated Dec. 18, 2014.

John Dellacontrada, "UB Engineers Develop Technology to Transmit Sensation of Touch Over the Internet", Jun. 23, 2003, p. 1-2.

* cited by examiner

METHOD AND APPARATUS FOR PROVIDING A HAPTIC MONITORING SYSTEM USING MULTIPLE SENSORS

RELATED APPLICATION

This application is related to the following co-pending application, each assigned to the Assignee of the present invention.

a. application Ser. No. 12/334,285, filed Dec. 12, 2008, entitled "Method and Apparatus for Providing a Haptic Monitoring System Using Multiple Sensors."

FIELD

The exemplary embodiment(s) of the present invention relates to the field of electronic communications. More specifically, the exemplary embodiment(s) of the present invention relates to communications using haptic feedbacks.

BACKGROUND

As computer-based systems, appliances, automated teller machines (ATM), point of sale terminals and the like become more prevalent, the ease of use with regard to the human-machine interface is becoming more important. Such interfaces should operate intuitively and require little or no user training whereby they may be employed by virtually anyone. Conventional human-machine interfaces, such as keyboard, voice, and touch screen, typically require human interactions involving a combination of action, vision and/or sound. For instance, when a user inputs his or her selection(s) over a touch screen, the user needs to look and identify a location on the screen for touching. Also, when a user operates a mouse, the user needs to see the mouse icon on the screen before clicking the mouse.

A problem, however, associated with conventional human-machine interfaces is that, for some situations and/or environments, an operator may not be able to use visual or audio capability to enter an input.

For example, in a healthcare environment, typical medical and health related monitoring/testing equipment used for monitoring and/or testing patients' vital signs notify caretakers such as nurses and doctors when the equipment detects certain predefined less-desirable conditions via visual and/or aural notifications. A typical heart rate monitor, for instance, shows a waveform of heart rate on a display with beeps indicating patient's heart beats. To discern a patient's condition, for example, a caretaker typically needs to look at the heart-rate waveform on the display or listen to the heart-rate beeps or both in order to observe patient's current condition. As such, a drawback associated with a conventional human-machine interface using aural and/or visual notifications is that the interface may be inadequate or inappropriate in some situations, such as in loud or visual cluttered situations, high-stress environments, social events like dinner parties, or entertainment venues such as poker games.

SUMMARY

The embodiment(s) of the present invention includes a haptic monitoring system capable of generating haptic feedback based on sensed information and method for making the same. The haptic system includes a sensing device, a digital processing unit, and a haptic generator. The sensing device is configured to selectively sense an individual's or user's vital information via one or more wearable sensors, and subsequently forwards the sensed vital information to the digital processing unit for data processing. Upon receipt of the vital information, the digital processing unit provides a haptic signal in response to the vital information. The haptic generator, subsequently, generates haptic feedback in accordance with the haptic signal. In an alternative embodiment, the haptic system further includes a positioning device capable of identifying the user's physical location.

Additional features and benefits of the exemplary embodiment(s) of the present invention will become apparent from the detailed description, figures and claims set forth below.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Embodiments of the present invention are described herein in the context of a method, system and apparatus for providing haptic cues in response to one or more events using an attachable or wearable haptic device.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the exemplary embodiments of the present invention as illustrated in the accompanying drawings. The same reference indicators (or numbers) will be used throughout the drawings and the following detailed description to refer to the same or like parts.

In the interest of clarity, not all of the standard hardware and routine features of the implementations described herein are shown and described. It will, of course, be understood that in the development of any such implementation, numerous implementation-specific decisions need to be made in order to achieve a developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The embodiment(s) of the present invention includes a haptic monitoring system capable of generating haptic feedback based on sensed information. The haptic system includes a sensing device, a digital processing unit, and a haptic generator. The sensing device can selectively sense an individual's or user's vital information via one or more wearable sensors, and subsequently forwards the sensed vital information to the digital processing unit for data processing. In an alternative embodiment, the sensing device also includes a position device which may employ a global position system to identify the physical location of the user. Upon receipt of the vital information, the digital processing unit provides a haptic signal in response to the vital information. The haptic generator, subsequently, generates haptic feedback in accordance with the haptic signal.

Figure 1:
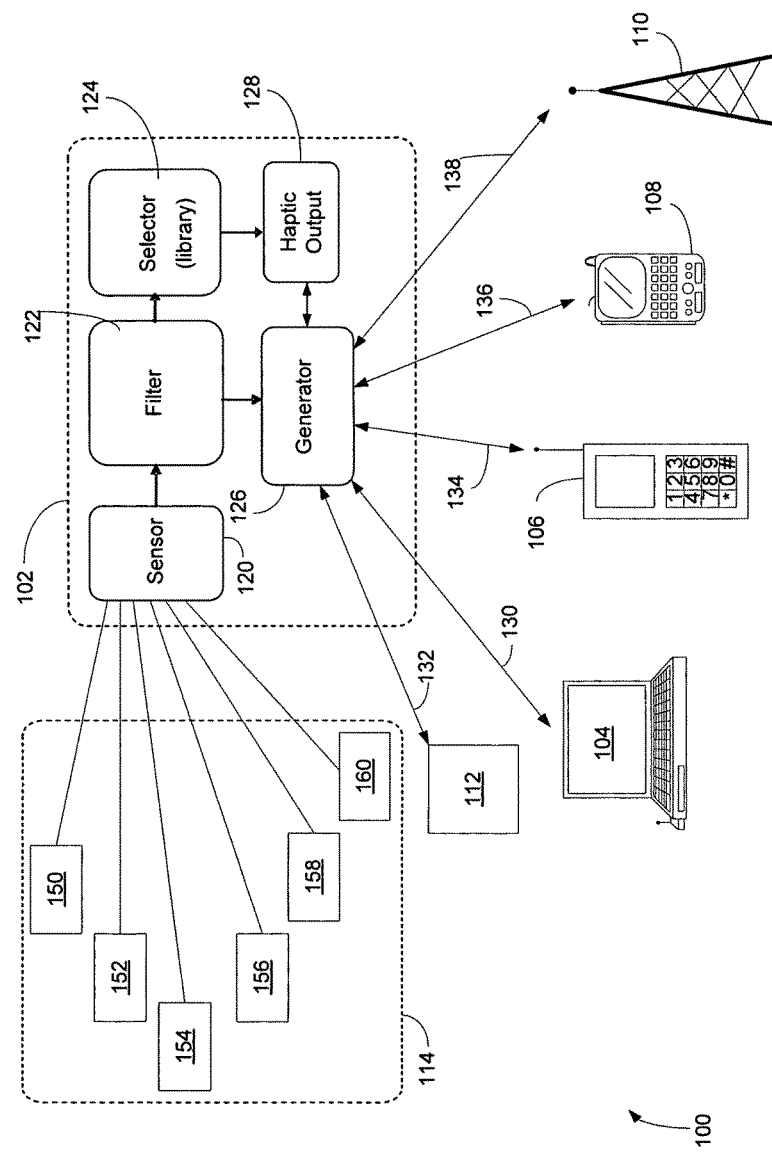
FIG. 1 is a diagram illustrating a haptic system capable of monitoring multiple events in accordance with one embodiment of the present invention.

FIG. 1 is a diagram 100 illustrating a haptic system capable of monitoring multiple events in accordance with one embodiment of the present invention. Diagram 100 includes a haptic wearable device 102, a computer 104, a cellular phone 106, a personal digital assistant ("PDA") 108, a communications network 110, and a sensing device 114. In one aspect, diagram 100 further includes an external computing processor 112, wherein processor 112 is capable of executing instructions for the haptic system. It should be noted that the underlying concept of the exemplary embodiment of the present invention would not change if additional blocks or devices were added to or removed from diagram 100.

Sensing device 114, in one embodiment, includes one or multiple sensors or sensing elements 150-160, wherein each of the sensors 150-160 can be selectively activated to monitor a specific vital sign (or information) of an individual. The individual can have a particular role such as a user, a patient, a client, a child, an athlete, a team member, group participant and so on. Sensors 150-160 can be attached to an individual via various attachment mechanisms such as wearing, fastening, implanting, and adhering. A function of sensor 150-160 is to read or monitor vital signs (or information) wherein the vital signs indicate various physiological statistics used for assessing basic body conditions. The vital signs, for instance, includes a body temperature, pulse rate (or heart rate), blood pressure, respiratory rate, and the like. Additionally, in an alternative embodiment the user's geographical location is determined.

Sensing device 114, in one embodiment, includes a heart rate monitor 150, a blood pressure monitor or sphygmomanometer 152, a breath sensor 154, a temperature gauge 156, a humidity sensor 158, and a motion detector 160 for monitoring the user's heart, blood pressure, respiration body temperature, body perspiration or location, respectively.

Sensors 150-160 can be fabricated or manufactured on a same unit. It should be noted that other sensors such as audio sensors to sense sound and/or weather sensors to detect ambient conditions, which can be used together with other vital sensors for obtaining vital data. Upon sensing the vital information, sensing device 114, in one embodiment, forwards the vital information to a digital processing unit via a communications network which can be wire, wireless, or a combination of wire and wireless networks.

Device 102, in one embodiment, includes a sensor 120, an internal filter 122, a selector 124, a generator 126, and a haptic output device 128. Device 102, in one example, can be structured as an ear piece, a wrist band, a necklace, a belt, a belt buckle, a watch, a watch band, a hat, or other appropriate structure. Sensor 120, in one example, may be a part of sensing device 114 responsible for interfacing between sensors 150-160 and device 102. Filter 122 is a circuitry filtering extraneous information such as unwanted movements and/or false pulses which can interfere with the detection of true vital signs (or desired information). In another embodiment, internal filter 122 can be located in a host computer, wherein the filtering process is implemented by a host processor, not shown in FIG. 1. Generator 126 generates commands (haptic signals) in response to the filtered vital signs or information, and subsequently, transmits commands and/or vital information to one or more destination devices such as computer 104 or PDA 108 via communication channels 132-138. It should be noted that the communication channels 132-138 can be wire, wireless, or a combination of wire and wireless communications networks.

Selector 124 includes one or more haptic libraries used for storing haptic data containing a list of haptic effects. In one embodiment, the list of haptic effects is used to provide a haptic feedback to a user in accordance with the detected vital information. Each vital sign detected, for example, may require a unique haptic feedback. It should be noted that the library containing haptic data can also be located in a remote host computer. In an alternative embodiment, haptic data can be dynamically generated and continuously updated to emulate and/or reproduce detected vital sign(s). To emulate vital signs in real-time, selector 124 is capable of dynamically generating haptic effect to emulate detected vital sign(s). For example, to track a bike racing team, each athlete on the bike racing team may carry a device to monitor and to reproduce or emulate the athlete's heart rate. The reproduced or emulated athlete's heart rate may be monitored by the athlete, coach, or any other interested parties. Haptic output device 128 generates haptic feedback in accordance with the haptic data selected by selector 124. For example, a mild vibration may emulate a calm condition or that the athlete is in the desired training or racing zone. A strong vibration may emulate a serious condition or that the athlete is not in the desired zone.

A function of device 102 is to provide and distribute haptic feedback as a communication channel to one or more devices, such as laptop 104, mobile or smart phone 106, PDA 108, network 110, and so on, at the same time. It should be noted that components 120-128 can also be located at several different entities depending on the applications. Device 102 can communicate with other devices 104-110 via cable connections, wireless connections, and a combination of cable and wireless networks. After sensing the vital information, it is subsequently forwarded to a digital processing unit for information processing.

The digital processing unit, in one embodiment, is an independent circuit, not shown in FIG. 1, in device 102.

Alternatively, the digital processing unit includes processor 112, filter 122, and selector 124. A function of the digital processing unit is to receive the vital information via a communications network and provide a haptic signal based on the vital information. In one embodiment, the digital processing unit includes a configurable software program which provides a range of predefined limitations for vital information or parameters. The range of predefined limitations indicates ranges of normal vital signs versus abnormal vital signs. After identifying the haptic signal, it is forwarded to a haptic generator.

The haptic generator which could be a part of haptic output device 128 is capable of receiving the haptic signal and generating haptic feedback in accordance with the haptic signal. In one embodiment, sensing device 114, the digital processing unit, and the haptic generator are installed or placed in the same unit. Alternatively, sensing device 114, the digital processing unit, and the haptic generator are logically connected via a circuit board, one or more wires and/or wireless communications networks.

Referring back to FIG. 1, the haptic system includes device, sensors, actuators/generator, or wearable components, wherein sensors are used to detect user vital or physical conditions while actuators are used to provide haptic feedback in accordance with the user conditions. The sensors and actuators, in one embodiment, can be constructed under the same device. For example, a heart rate sensor senses a user's heart rate processes the heart rate and generates a series of haptic feedback to indicate the current user's physical condition. It should be noted that the term haptic feedback can be referred to as tactile effect, tactile feedback, haptic effect, force feedback, vibrotactile feedback, haptic cues, and so forth.

Some haptic materials such as piezoelectric material have the physical property of sensing as well as providing vibrotactile effect. For example, piezoelectric material discharges a current indicating that it detected a pressure when its physical shape deforms due to pressure. Piezoelectric materials, in one embodiment, include crystals and/or ceramics such as quartz ($SiO_2$). When a voltage potential applies to the piezoelectric material, it deforms from its original shape to an expanded shape. Piezoelectric material may return to its original state as soon as the voltage potential is removed. Piezoelectric material, however, releases a current when it is being pressed. As a result, piezoelectric material can detect an input when it is being pressed. Vibrotactile feedback or haptic feedback may be provided through a piezo material, shape memory alloy ("SMA"), eccentric rotating mass ("ERM") or linear resonant actuator ("LRA"), or the like. Similar functions of sensor/actuator may be performed if the piezoelectric material is replaced with other materials or devices, such as LRA, ERM, and SMA. SMA, in one example, is capable of maintaining its deformed shape for a period of time after the voltage potential is removed. It should be noted that the underlying concept of the embodiments of the present invention does not change if different materials are employed. Device 102 is applicable to an individual or a team to identify the physical condition of an individual, a team member or the overall team. For example, device 102 may inform one of the cyclists to speed up or slow down to improve team performance in accordance with detected psychological condition. It should be noted that device 102 can also be used for other applications such as those discussed below. The haptic system, in one embodiment, can include multiple units wherein some of the units are located in the chest, wrist, foot, and/or the like to sense user's vital signs. Haptic generator 128, for example, is capable of generating haptic cues or haptic warning signals at different levels of intensities for different levels of physical fitness and/or performance. For example, haptic generator 128 generates a minor haptic cue when user's performance is slightly below the optimal performance level, and generates an intensified haptic cue when user's performance is below the minimal acceptable level. It should be noted that using tactile feedback to indicate the user's physical conditions can be a subtle, discreet, and non-intrusive communication method.

Device 102, sensing device 114, and computer 104 are capable of communicating between the devices via network 110 which may include wire and wireless communications networks. The wireless communications network may include local radio frequencies, Bluetooth, cellular (GPRS, CDMA, GSM, CDPD, 2.5G, 3G, etc.), Ultra-Wideband (UWB), WiMax, ZigBee, and/or other ad-hoc/mesh wireless network technologies. To reduce power consumption, a relay station can be placed in the network to relay haptic signals through other haptic devices.

An advantage of employing a haptic system is to create essentially a communication channel to transmit information between a user and a machine. The haptic system has various applications, such as communications between multiple parties, sports teams, military missions, and the like.

Figure 2:
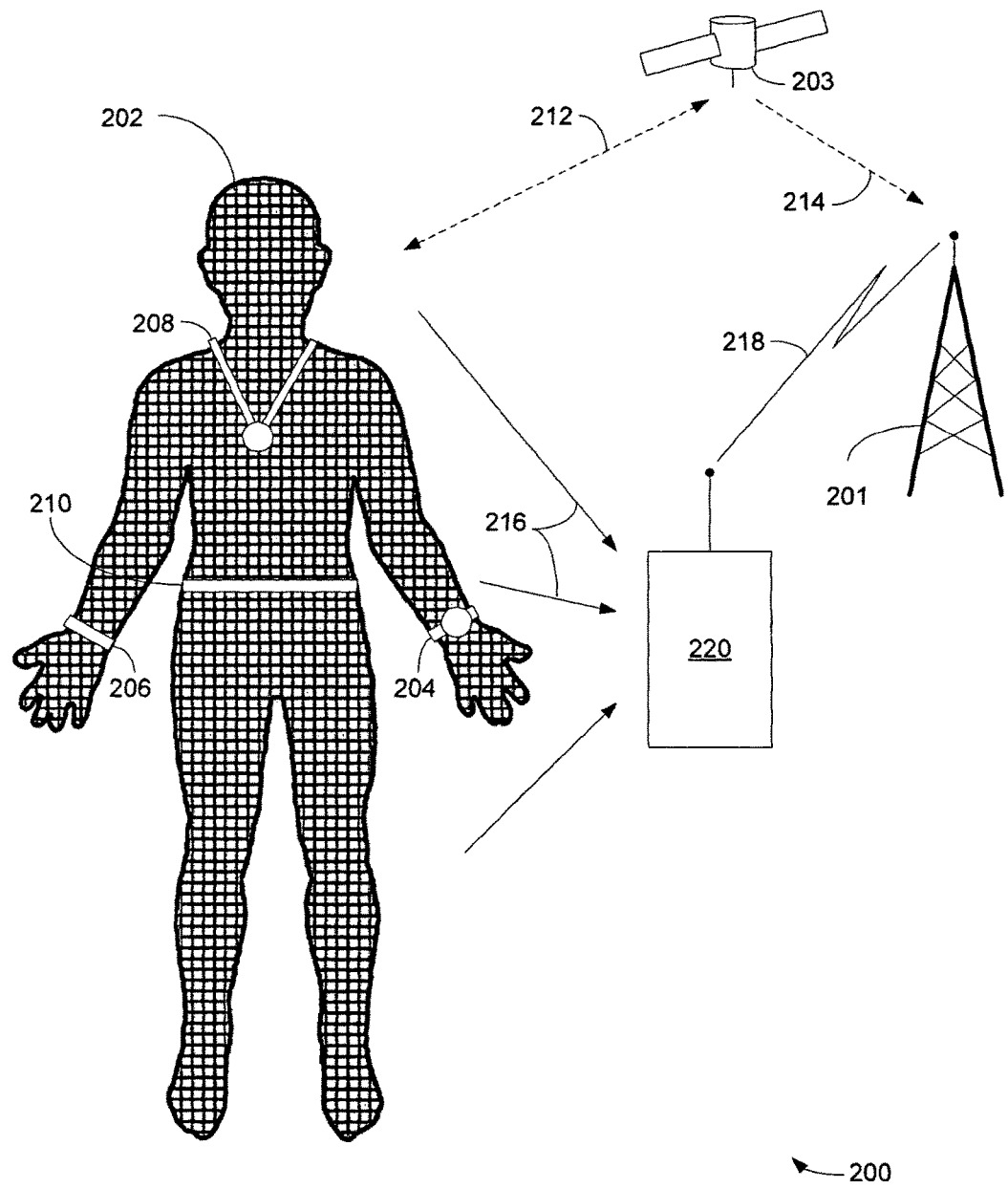
FIG. 2 is a diagram illustrating a human wearing multiple sensors for collecting event information in accordance with one embodiment of the present invention.

FIG. 2 is a diagram 200 illustrating a human wearing multiple sensors for collecting event information in accordance with one embodiment of the present invention. Diagram 200 shows an exemplary feedback monitoring device including a person 202, a network 201, and a global positioning system ("GPS") satellite 203. In one embodiment, person 202 and network 201 can communicate via one or more communications networks, such as a wireless communications network, an Internet, a personal area network, a local area network, a metropolitan area network, a wide area network, and so forth. It should be noted that the underlying concept of the exemplary embodiment of the present invention would not change if additional blocks and/or devices were added to or removed from diagram 200.

Person 202, in one embodiment, wears one or more haptic wearable devices 204-210 wherein some of the devices could be sensors for obtaining vital signs of person 202. For example, wearable device 204 is a wrist watch which is capable of monitoring pulse rate and providing haptic cue(s). Wearable device 210 is a haptic belt capable of detecting user's respiratory rate while wearable device 208 is a haptic necklace capable of detecting user's blood pressure. Also, wearable device 206 may be a wrist band used for sensing user's humidity and/or moisture perspiration. Wearable devices 204-210, in this embodiment, are capable of generating haptic feedback or cue(s) at the same time they provide monitoring functions.

In one embodiment, person 202 carrying a GPS device capable of providing real-time physical location of person 202. For example, the GPS device, which could be installed at necklace 208, communicates with satellite 203 via radio frequencies 212-214 to identify real-time location of person 202. After collecting vital signs via wireless signals 216, a processor 220 analyzes physical condition and performance of person 202 based on the detected vital signs as well as location, and provides adjustment(s) to enhance the performance of a team sport. It should be noted that processor 220 can be located locally or remotely.

Haptic wearable device(s) 204, 206, 208, or 210 is also applicable to other mammals as well as machinery or inanimate object(s) such as dogs, cats, cars, or engines. For example, to enhance horse race performance, a jockey may use a haptic wearable device to monitor horse's heart rate. A race car driver or pit crew chief, for example, may receive haptic output relating to mechanical conditions of the car, such as engine temperature and tire traction.

Referring back to FIG. 2, a haptic system includes a sensing device, a positioning device, a digital processing unit, and a haptic generator. The sensing device, which could include one or more wearable devices 204-210, can be selectively set to sense vital physical sign(s) or information of person 202 via sensors. The sensing device, in one embodiment, includes a heart rate sensor, a motion sensor, a blood pressure sensor, a breath sensor, a temperature sensor, and a humidity sensor. It should be noted that the sensing device can also include a sensor communication block which facilitates communications between sensors via one or more wire or wireless communications networks.

The positioning device, in one embodiment, is coupled to the sensing device and configured to identify user's physical location. The positioning device, for example, includes GPS circuitry capable of identifying location, speed, direction, and time associated with the user or person 202. Upon obtaining GPS data via satellite 203, GPS data are forwarded to the digital processing unit for processing.

Upon receipt of vital and GPS information, the digital processing unit subsequently provides a haptic signal in response to the vital physical information and user's physical location. Depending on the applications, the digital processing unit can generate multiple haptic signals to emulate more realistic sensations. The digital processing unit, in one example, includes configurable software capable of storing predefined limitations for various performance parameters associated with vital information. These parameters can be general or specific to the individual or activity in question. The haptic signal(s), also known as haptic input(s), is subsequently forwarded to the haptic generator.

It should be noted that the haptic system can be used as an attachable coordination device capable of providing haptic cues to coordinate military or combat actions. Also, the wearable performance enhancer can improve team performance by providing haptic cues to increase each team member's physical performance during a team sport such as a team cycling or a water polo competition.

Figure 3:
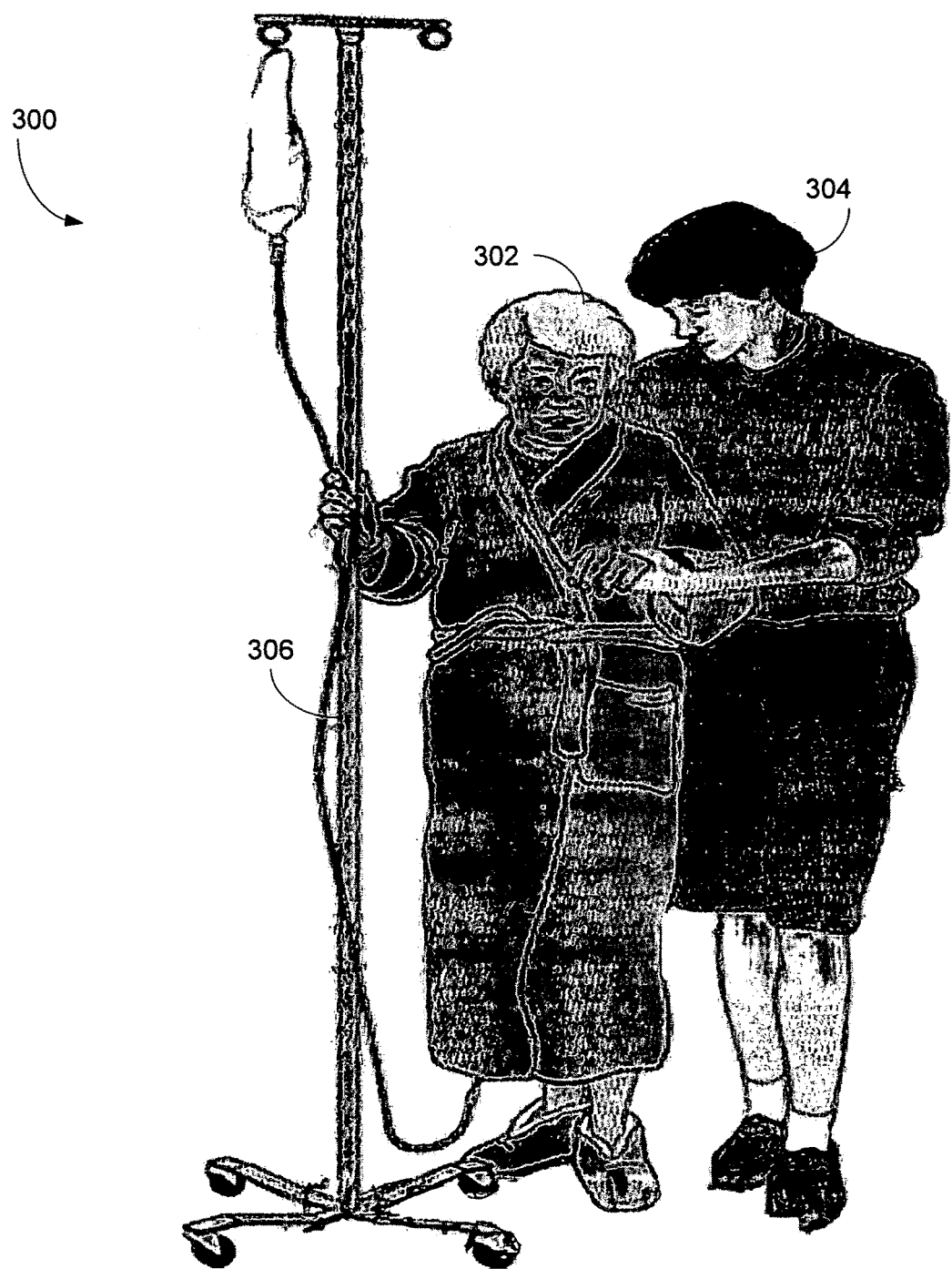
FIG. 3 is a diagram illustrating a haptic health monitor in accordance with one embodiment of the present invention.

FIG. 3 is a diagram 300 illustrating a haptic health monitor in accordance with one embodiment of the present invention. Diagram 300 includes a patient 302, a nurse 304, and an intravenous ("IV") stand 306. In one embodiment, IV stand 306 includes a haptic health monitor which provides real-time sensing capabilities. It should be noted that the underlying concept of the exemplary embodiment of the present invention would not change if additional blocks and/or devices were added to or removed from diagram 300.

Patient 302, for instance, suffers a medical condition, such as a heart disease, a respiratory disease, high blood pressure, et cetera, and she needs to be under constant observation. Patient 302, in one embodiment, wears a haptic health monitor which reads vital signs of patient 302 on a continuous basis. After observing the vital signs, the haptic health monitor distributes the information relating to the vital signs to patient 302, nurse 304, and/or other interested parties. The haptic health monitor, in one example, can be installed in IV stand 306 thereby the monitor is capable of detecting and recording vital signs of patient 302 as long as patient 302 is in contact with or nearby IV stand 306. Alternatively, patient 302 can wear different wearable haptic health device(s), not shown in FIG. 3, under her gown.

The haptic health monitor, in one embodiment, includes sensing capabilities, calibrating features, and haptic feedback. For example, a haptic health monitor includes configurable and/or calibrating software that facilitates a procedure(s) of when and how the haptic alerts should be triggered. After setting up a monitoring procedure for a particular patient, one or more sensors on the monitor read the vital statistics of an individual or patient 302 in accordance with the monitoring procedure. Upon processing the vital statistics, electronics and actuator(s) within the monitor send a haptic event or haptic feedback to patient 302, nurse 304, or others in response to the vital statistics. It should be noted that haptic feedback or haptic cues generated in accordance with alert(s) may or may not include aural or visual alert components.

The haptic health monitor is particularly helpful for hospital patients as well as released patients. For patients suffering, for example, hemophiliacs or heart diseases, they or their caretakers need to be alerted or notified as soon as there is marked drop or increase in patient heart rate. Hemophiliacs can benefit greatly from an alert as it might alert them to the fact that they had been cut and were unaware. Heart patients can also benefit from being alerted upon detecting an abnormally high or low blood pressure. Haptic feedback generated in accordance with the alerts can indicate that medical attention is necessary.

An advantage of employing the haptic health monitor is to provide an alternative channel of communication. Haptic feedback can be effective under certain environmental unfriendly situations. For example, haptic feedback tends to work well in a noisy environment that precludes audio alerts. A haptic health monitor and alerter can also be useful for individuals working in high pressure position, as well as some recreational leisure activities.

Figure 4:
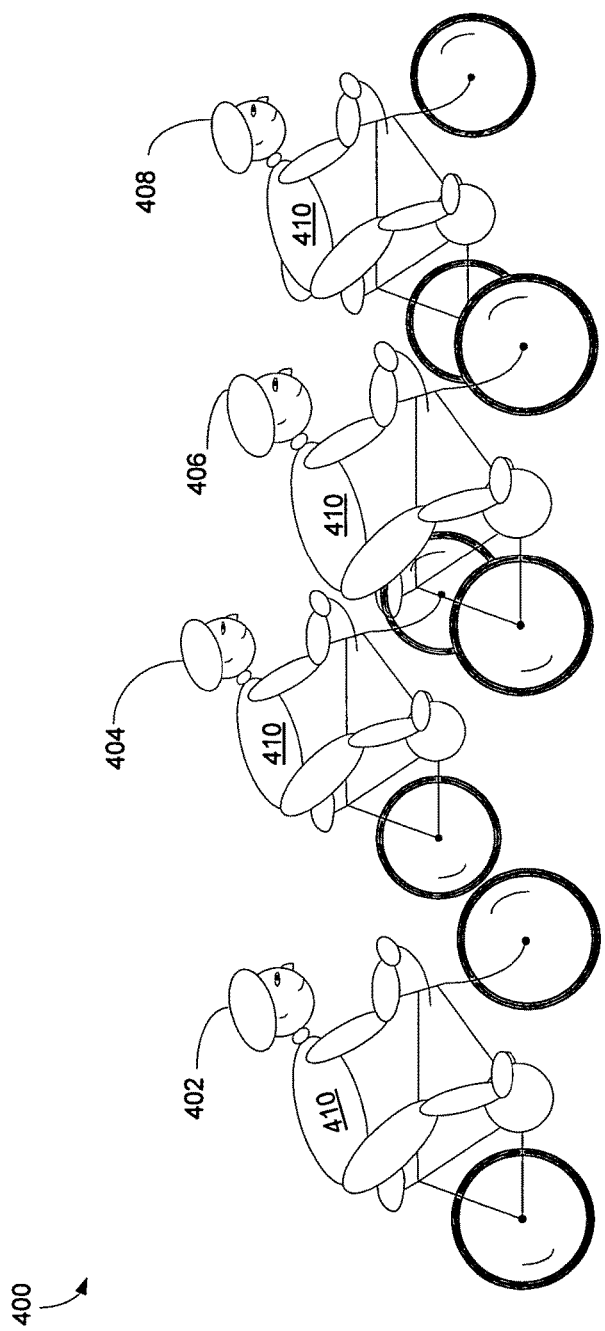
FIG. 4 illustrates a cycling team wearing haptic enhancing devices in accordance with one embodiment of the present invention.

FIG. 4 is a diagram 400 illustrating a cycling team wearing haptic enhancing devices in accordance with one embodiment of the present invention. Diagram 400 illustrates a cycling team having four (4) cyclists 402-408 with four (4) bikes. In one embodiment, each cyclist wears a haptic coordinating and enhancing device 410. Each device 410 senses the vital signs of the cyclist who carries the device and coordinates with other devices 410 to enhance the team performance. It should be noted that the underlying concept of the exemplary embodiment of the present invention would not change if additional blocks or devices were added to or removed from diagram 400.

Each cyclist or athlete in general can benefit from the application of haptic enhancing device to improve individual as well as team performance. Note that cardiovascular intensive activities that take place over an extended period time can benefit from constant monitor of heart rate. For example, a haptic monitor providing feedback to an athlete facilitates a better race management strategy as well as suggesting level of energy to be exerted. Heart rate information, for example, can provide information relating to $VO_2$ (maximal oxygen consumption) which is the maximum capacity of a body to consume oxygen during an extraneous physical exercise. $VO_2$, also known as maximum volume of oxygen in milliliters, is a measurement used by sports activities.

Haptic coordinating and enhancing device 410, for example, includes a positioning block circuit capable of communicating with a GPS system for identifying the physical location of each bike. Upon analyzing the data relating to physical locations of each bike and vital statistics of every cyclist, haptic coordinating and enhancing device 410 can instruct cyclist 402 to take the position of cyclist 408 for improving the team performance. It should be noted that haptic coordinating and enhancing device 410 can be applied to various types of team sports, such as football, water polo, and/or basketball teams.

Figure 5A:
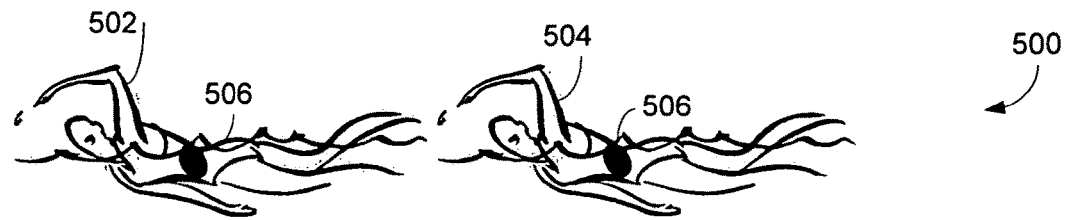
FIG. 5A is a diagram illustrating an exemplary application to a team of water polo swimmers having haptic enhancing devices in accordance with one embodiment of the present invention.

FIG. 5A is a diagram 500 illustrating an exemplary application to a team of water polo swimmers having haptic enhancing devices in accordance with one embodiment of the present invention. Diagram 500 includes a first swimmer 502 and a second swimmer 504 wherein each swimmer wears a haptic enhancing device 506. Devices 506, in one embodiment, monitor and record every swimmer's vital signs as well as his or her physical location via a GPS device. Device(s) 506, for example, generates haptic feedback or cue indicating the fatigue level of swimmer 504 when the performance analysis of swimmer 504 falls below a predefined acceptable performance level in response to the collected vital information. The haptic feedback or cue can be transmitted to the swimmer who wears device 506, or to other interested parties, such as coaches, trainers, or teammates.

Figure 5B:
FIG. 5B is a diagram illustrating an exemplary application to a poker player having a haptic monitoring device in accordance with one embodiment of the present invention.

FIG. 5B is a diagram 550 illustrating an exemplary application to a poker player having a haptic monitoring device in accordance with one embodiment of the present invention. Diagram 550 includes a poker player 552 who wears a haptic monitoring device 510. Device 510 can be configured to monitor vital signs of poker player 552 and is capable of providing a haptic alert to player 552 if certain vital signs reach an undesirable range. For example, poker player 552 can set a limitation of heart rate to 150 and the heart rate monitor will provide a haptic alert to notify player 552 that his or her heart rate has reached the limit. It should be noted that high stakes card or poker players will appreciate silent alarms indicating their heart rates. Keeping a lower heart rate and staying calm can be critical at poker table to avoid any facial and/or gesture detections by the opponents.

Haptic cue or alert in accordance with vital signs is also applicable in a medical condition of pregnancy. For example, a pregnant woman can feel fetal heart beats via a heart rate monitor which allows mother to feel fetal heart rate via haptic cues. The pregnant woman can take certain precautions depending on the fetal heat beats. Alternatively, fetal vital signs can also be transmitted to the doctor's (obstetrician or gynecologist) office on a periodic basis. It should be noted that the report to the doctor's office can occur automatically via a wireless communications network.

Haptic cues or alerts in accordance with vital signs can also be applicable in other situations such as sporting contests. For example, during a biathlon contest, each athlete skis (or runs) for a distance, and then shoots the target(s) later. If an athlete wears a haptic coordinating and enhancing device, it can optimize athlete's physical condition to have a most desirable speed in skiing while being sufficiently calm to aim at the target.

Haptic cues or alerts in accordance with vital signs are also applicable in other situations such as for machine operators. For example, air force pilots pulling high velocity and gravity maneuvers can be alerted in the event that their accelerations have reached the threshold of G-suits worn by the pilots. It should be noted that haptic cue and alert device can also apply to situations such as high-speed car racers or deep-sea divers.

Figure 6:
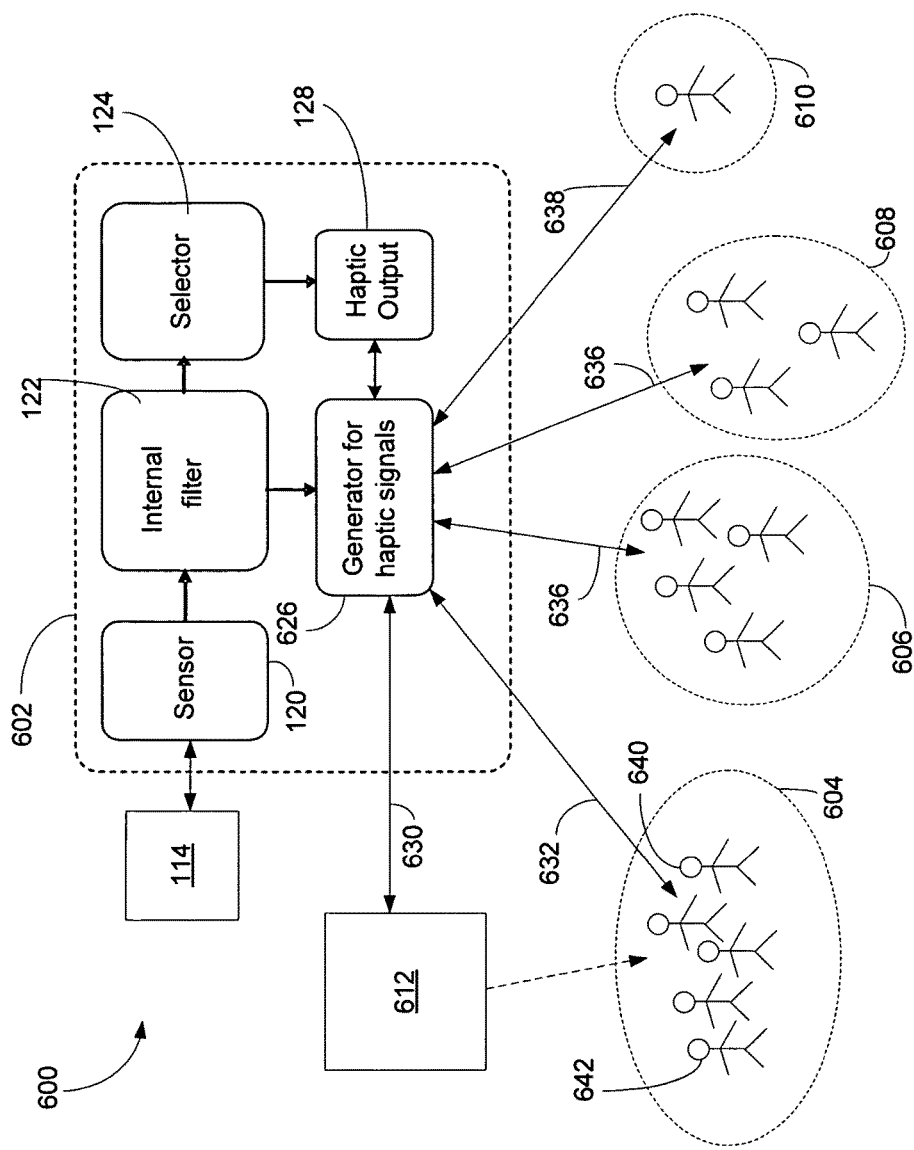
FIG. 6 is a diagram illustrating several groups of people organized by a coordinating haptic device in accordance with one embodiment of the present invention.

FIG. 6 is a diagram 600 illustrating several groups of people organized by a coordinating haptic device in accordance with one embodiment of the present invention. Diagram 600 includes a wearable or attachable haptic device 602, a first group of people 604, a second group of people 606, a third group of people 608, a fourth group of people 610, and a relay station 612, which is capable of amplifying and relaying haptic signals. It should be noted that the underlying concept of the exemplary embodiment of the present invention would not change if additional blocks such as power supply were added to or removed from diagram 600.

Each group of people may encompass a unique characteristic, and each group of people may transmit or receive a specific set of haptic signals. For example, first group 604 includes a group of special force soldiers 642, while second group 606 includes a group of military service soldiers for backup. Third group 608 includes a group of soldier decoys, while fourth group 610 includes the commanding officer. Each person in groups 604-610 wears a haptic coordinating device, where the haptic device is used to provide a silent channel of communication. For example, the commanding officer can sense the soldiers physical status in real-time via their vital signs.

Wearable haptic device 602, similar to device 102 illustrated in FIG. 1, includes a sensor 120, an internal filter 122, a selector 124, a generator 626, and a haptic output device 128. Sensor 120 is configured to sense vital signs and filter 122 is used to remove extraneous information, which is not relevant to the vital signs. Selector 124 selects one haptic cue from a group of stored haptic effects. Device output device 128 is an actuator capable of generating haptic feedback in accordance with the information received from selector 124. It should be noted that communications 632-638 between the groups and device 602 can be wire or wireless communications networks.

In a combat situation, it is important to know the availability of your own force regarding their current physical situations and locations. For example, physical situations can indicate number of alive, injured, and dead soldiers. Physical locations can indicate whether the soldiers are within striking distance. Also, combat medics could be informed of a soldier's need for medical attention. It should be noted that haptic feedback for medical attention of soldiers can be generated based on reading of group's vital statistics and their physical locations.

Figure 7:
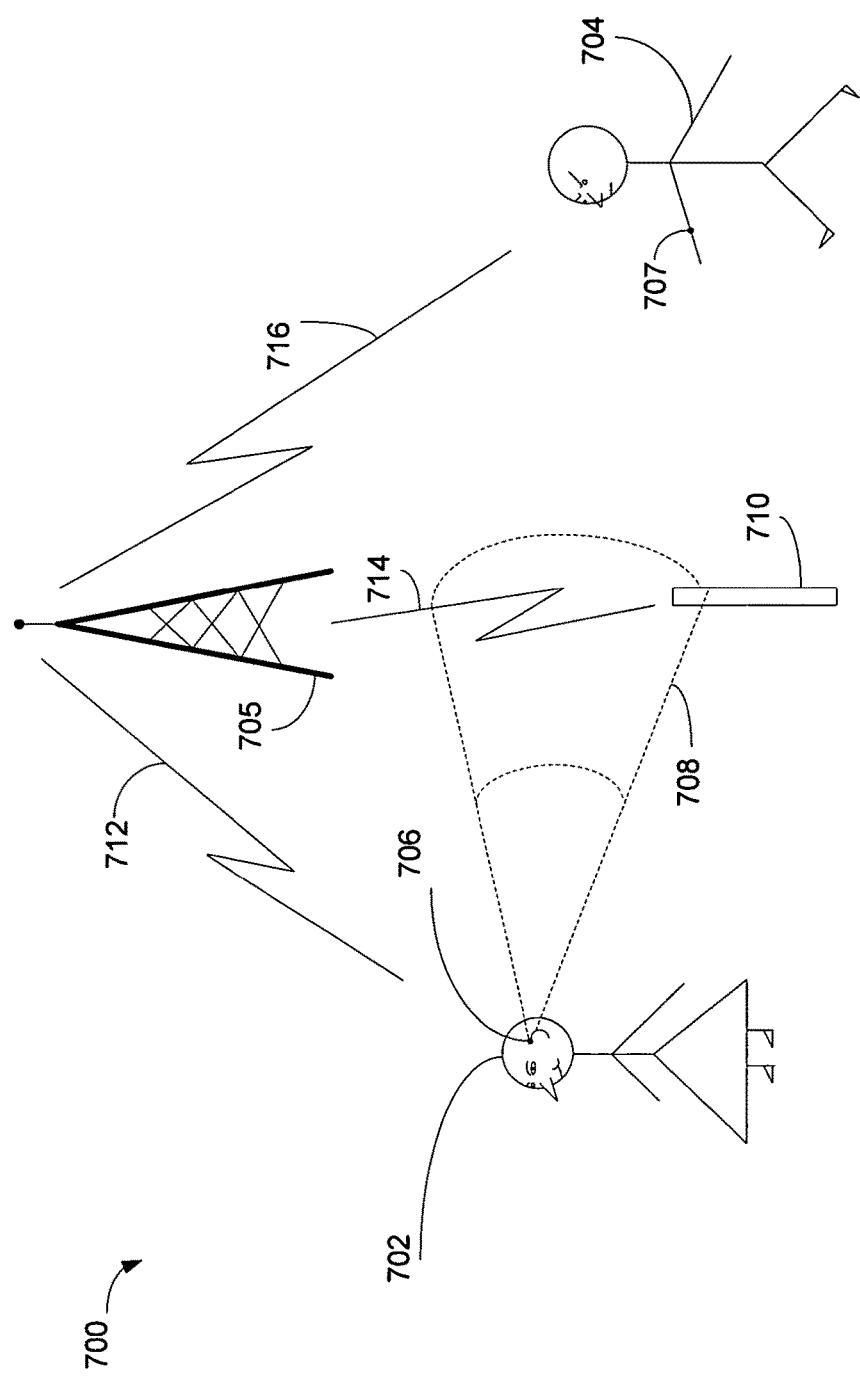
FIG. 7 is a diagram illustrating a person wearing a haptic alert device in accordance with one embodiment of the present invention.

FIG. 7 is a diagram 700 illustrating a person wearing a haptic alert device in accordance with one embodiment of the present invention. Diagram 700 includes a child 702, a teacher 704, and a network system 705. Child 702, in one embodiment, wears a haptic alert device 706 capable of providing haptic alert. Teacher 704 carries a haptic alert device 707, wherein devices 706 and 707 can communicate through one or more wireless signals 712 and 716 via network 705. It should be noted that the underlying concept of the exemplary embodiment of the present invention would not change if additional blocks were added to or removed from diagram 700.

Haptic alert device 706, in one embodiment, includes a locating or positioning block capable of broadcasting an alert signal when an event is detected. For example, RF (radio frequency) technology may be used together with the haptic technology to alert a teacher when a child or a pupil has walked out of school premises. For example, when a child worn device 706 walks passing a RF post 710 which immediately detects a radio frequency 708 emitted from device 706, RF post 710 issues a warning signal indicating child 702 has passed post 710 to teacher 704 via network 705 using wireless signals 714. Upon receipt of warning signal, haptic device 707 carried by teacher 704 sends a silent haptic cue informing teach 704 that child 702 is walking out of school campus. It should be noted that silent haptic communication channel in some situations is more effective than ordinary communication channels such as visual and audio. For example, teachers or pre-school staff in a loud campus and/or a busy playground can be alerted via a silent vibrotactile signal.

Haptic alert device 706 can be applied to other situations for providing haptic alert and/or feedback. For example, device 706 can be used to alert caretakers when their patients, disabled, impeded or elderly persons require medical or physical attention. For example, when a haptic monitor is able to monitor a person's vertical and horizontal orientation, it can issue a haptic alert of requiring medical attention when it detects a falling person on the ground or floor.

The exemplary embodiment(s) of the present invention includes various processing steps, which will be described below. The steps of the embodiments may be embodied in machine or computer executable instructions. The instructions can be used to cause a general purpose or special purpose system, which is programmed with the instructions, to perform the steps of the present invention. Alternatively, the steps of the present invention may be performed by specific hardware components that contain hard-wired logic for performing the steps, or by any combination of programmed computer components and custom hardware components.

Figure 8:
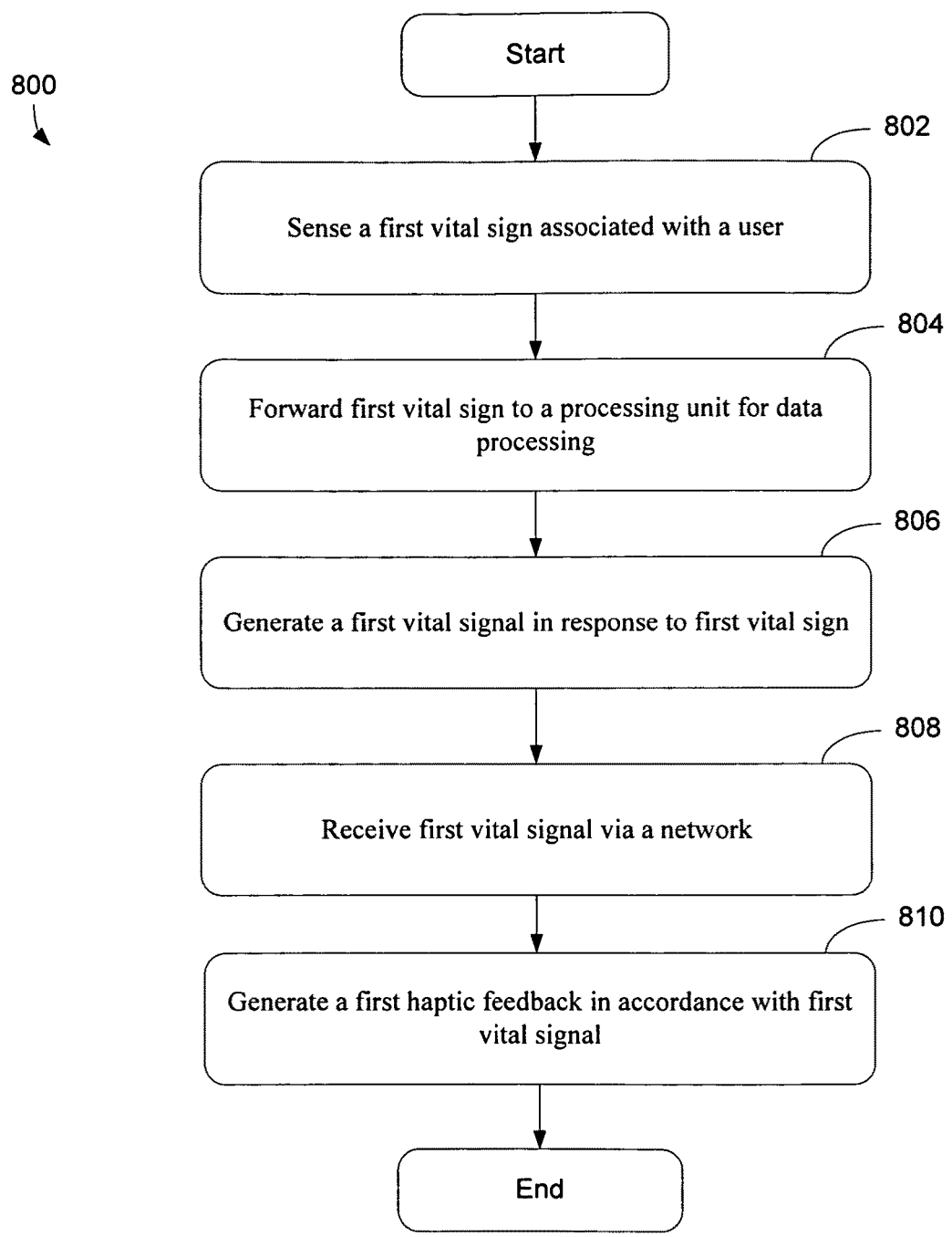
FIG. 8 is a flowchart illustrating a process of providing haptic health feedback in response to one or more events in accordance with one embodiment of the present invention.

FIG. 8 is a flowchart 800 illustrating a process of providing haptic health feedback in response to one or more events in accordance with one embodiment of the present invention. At block 802, a process is capable of sensing a first vital sign associated with a user. The user, for instance, is a person who wears or carries the haptic device. In one embodiment, the process is capable of sensing a second vital sign associated with the user. For example, a heart rate can be detected by a heart rate monitor and user's blood pressure can be measured by a blood pressure monitor. In an alternative embodiment, the process is further configured to detect user's respiratory rate via a breath sensor and read user's body temperature via a temperature gauge.

At block 804, the process forwards the first vital sign and/or second vital sign to a processing unit for data processing. It should be noted that the processing unit can be an onboard processor or a remote processor.

At block 806, the process generates a first vital signal in response to the first vital sign and a second vital signal in response to the second vital sign. Depending on the vital sign(s), different haptic effect signals generate different haptic sensations.

At block 808, the process is capable of receiving the first vital signal and the second vital signal via a network. It should be noted that the process can receive and process additional vital signs and generate additional vital or haptic signals.

At block 810, the process is capable of generating a first haptic feedback in accordance with the first vital signal and a second haptic feedback in accordance with the second vital signal. In one embodiment, the process can generate a haptic cue in response to the first haptic feedback and the second haptic feedback. Also, the process provides a haptic cue to indicate a fetal heart beat. The process can also provide a haptic cue to indicate current heart condition. Furthermore, the process can provide a haptic cue to indicate a real-time sugar level in user's blood. In another embodiment, the process can provide a haptic cue to indicate current level of blood pressure. In yet another embodiment, the process is capable of providing a haptic cue to indicate a real-time bleeding condition of hemophilia.

Figure 9:
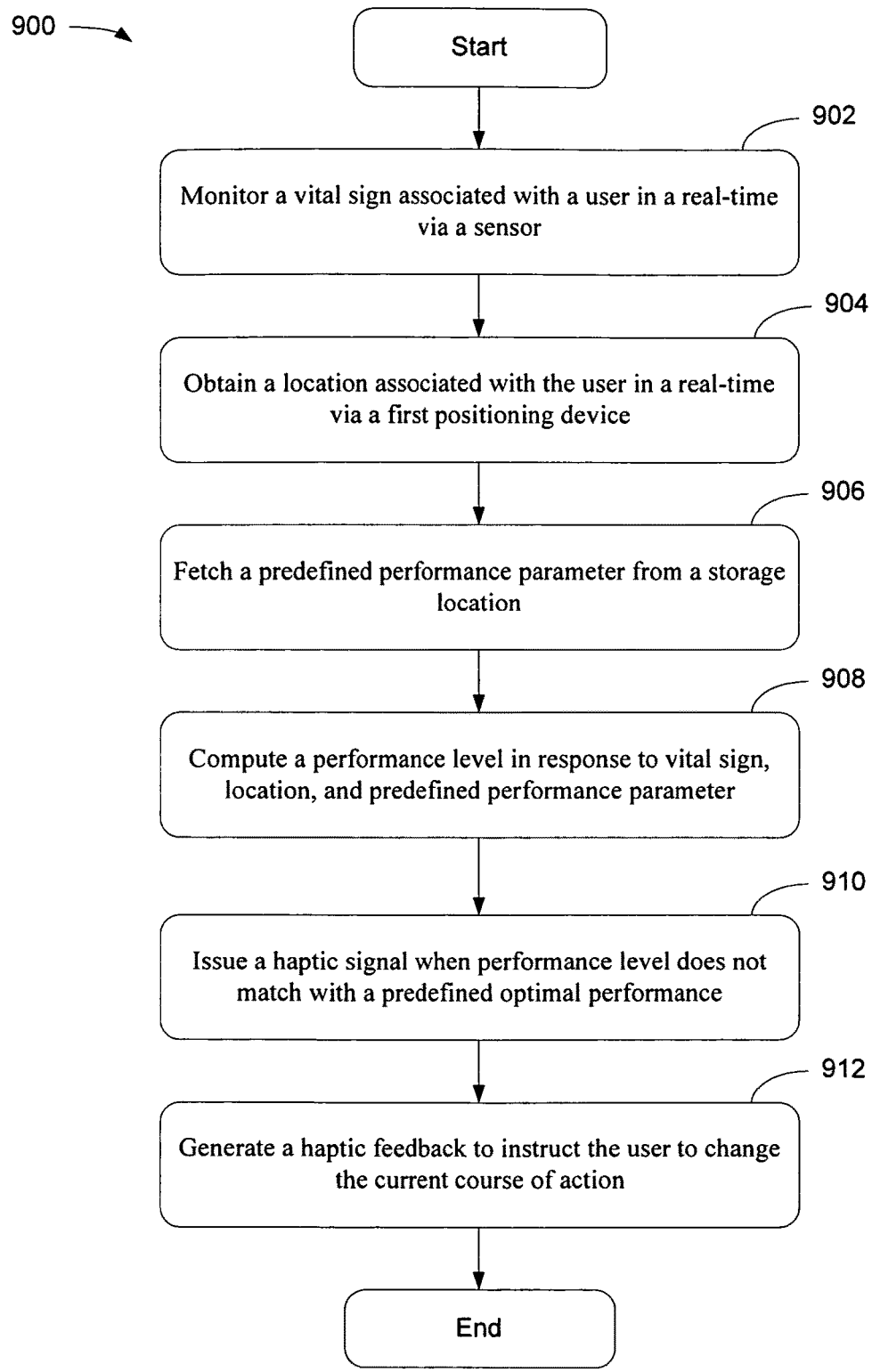
FIG. 9 is a flowchart illustrating a process of providing haptic coordinating feedback in response to one or more events in accordance with one embodiment of the present invention.

FIG. 9 is a flowchart 900 illustrating a process of providing haptic coordinating feedback based on events in accordance with one embodiment of the present invention. At block 902, a process monitors a first vital sign associated with a first user in a real-time via a first sensor and a second vital sign associated with a second user in a real-time via a second sensor. The process subsequently forwards the vital sign to a processing unit for data processing. In one embodiment, the process is configured to read a heart rate utilizing a heart rate monitor. The process is also able to read first user's blood pressure via a blood pressure monitor. In another embodiment, the process is also able to detect user's respiration via a breath sensor. Alternatively, a body temperature can also be read by a temperature gauge.

At block 904, the process obtains a first location associated with the first user in a real-time via a first positioning device and a second location associated with the second user in a real-time via a second positioning device. It should be noted that the first and second persons can be the same person.

At block 906, the process fetches a first predefined performance parameter from a storage location and a second predefined performance parameter from the storage location. The predefined performance parameters can be entered and stored by the user.

At block 908, the process is capable of computing a first performance level in response to the first vital sign, the first location, and the first predefined performance parameter. The process is further capable of computing a second performance level in response to the second vital sign, the second location, and the second predefined performance parameter.

At block 910, the process issues a first haptic signal when the first performance level does not match with a predefined optimal performance. Alternatively, the process issues a second haptic signal when the second performance level does not match with a predefined optimal performance.

At block 912, the process generates a first haptic feedback to instruct the first user to change current course of action and a second haptic feedback to instruct the second user to change current course of action. The process is able to generate a first haptic cue in response to the first haptic signal and a second haptic feedback and a second haptic cue in response to the first haptic signal and the second haptic signal. In one embodiment, the process is capable of instructing the first user to take over the second user's position. In addition, the process is able to inform the second user regarding the location of the first user. In one embodiment, the process is capable of providing a haptic cue to indicate current level of blood pressure. Alternatively, the process is capable of providing a haptic cue to indicate a real-time bleeding condition of hemophiliac.

While particular embodiments of the present invention have been shown and described, it will be obvious to those skills in the art that, based upon the teachings herein, changes and modifications may be made without departing from this invention and its broader aspects. Therefore, the appended claims are intended to encompass within their scope all such changes and modifications as are within the true spirit and scope of the exemplary embodiment(s) of is present invention.

What is claimed is:

1. A haptic system, comprising:
 a sensing device configured to receive vital physical information and extraneous movement information from a first user, the vital physical information comprising a plurality of vital signs;

a filtering device configured to isolate the vital physical information from the extraneous movement information and to discard the extraneous movement information;

a selector configured to dynamically generate haptic data that emulates the vital physical information isolated from the extraneous movement information of the first user; and a haptic generator configured to generate a first haptic feedback based on the dynamically generated haptic data, wherein the first haptic feedback is unique for each type of the plurality of vital signs, wherein a strength of the first haptic feedback is varied according to whether a first vital information is within a first desired zone.

2. The haptic system of claim 1, further comprising one or more sensors associated with the first user, the one or more sensors comprising:

a heart rate sensor configured to sense a heart rate;

a motion sensor configured to detect body movements; and a blood pressure sensor configured to read an individual's blood pressure.

3. The haptic system of claim 1, further comprising one or more sensors associated with the first user, the one or more sensors comprising:

a breath sensor operable to detect air respiration;

a temperature sensor operable to read body temperature; and a humidity sensor configured to sense body moisture perspiration.

4. The haptic system of claim 1, further comprising:

one or more sensors associated with the first user, wherein each sensor communicates with other sensors via a wireless network; and a transceiver operable to transmit the vital physical information or physical location information associated with the first user via a wireless communications network.

5. The haptic system of claim 1, further comprising a positioning device configured to identify physical location information associated with the first user.

6. The haptic system of claim 5, further comprising a digital processing unit configured to store predefined limitations for at least some of the vital physical information or physical location information received from the first user.

7. The haptic system of claim 5, wherein the haptic generator is further configured to generate a haptic signal based on the vital physical information or the physical location information from the first user and communicate the haptic signal to a device remote from the haptic generator.

8. The haptic system of claim 7, wherein the haptic generator is configured to communicate the haptic signal to the first user.

9. The haptic system of claim 7, further comprising:

a relay station communicatively coupled to the haptic generator, the relay station configured to amplify and relay the haptic signal to a second user.

10. The haptic system of claim 5, wherein the selector is further configured to: select the haptic data based on the physical location information from the first user.

11. The haptic system of claim 5, wherein the selector is further configured to:

select, from a first set of haptic data, a first haptic signal based on the vital physical information or the physical location information from the first user, and select, from a second set of haptic data, a second haptic signal based on vital physical information or physical location information from a second user, the second set of haptic data being distinct from the first set of haptic data.

12. The haptic system of claim 1, wherein the haptic generator is further configured to:

generate a second haptic feedback to a second user based on the selected haptic data, the second haptic feedback being different from the first haptic feedback.

13. The haptic system of claim 1, further comprising one or more sensors connected by a personal area network.

14. The haptic system of claim 1, wherein the sensing device and the haptic generator are disposed in a single device that simultaneously executes sensing and haptic functions.

15. The haptic system of claim 1, wherein the first haptic feedback emulates a characteristic of the vital physical information.

16. The haptic system of claim 1, wherein the extraneous movement information includes unwanted movements.

17. A method, comprising:

receiving, by a sensing device, vital physical information and extraneous movement information from a first user, the vital physical information comprising a plurality of vital signs;

isolating, by a filtering device, the vital physical information from the extraneous movement information and discarding the extraneous movement information;

dynamically generating, by a selector, haptic data that emulates the vital physical information isolated from the extraneous movement information of the first user;

generating, by a haptic generator, a first haptic feedback based on the dynamically generated haptic data, wherein the first haptic feedback is unique for each type of the plurality of vital signs; and varying a strength of the first haptic feedback according to whether the first vital information is within a first desired zone.

18. The method according to claim 17, wherein the vital physical information includes one of heart rate, blood pressure, body temperature, or body moisture.

19. The method according to claim 17, further comprising identifying a physical location associated with the first user.

20. The method according to claim 17, wherein the first haptic feedback emulates a characteristic of the vital physical information.

21. A non-transitory computer readable storage medium storing one or more programs configured to be executed by a processor, the one or more programs comprising instructions for:

receiving, by a sensing device, vital physical information and extraneous movement information from a first user, the vital physical information comprising a plurality of vital signs;

isolating, by a filtering device, the vital physical information from the extraneous movement information and discarding the extraneous movement information;

dynamically generating, by a selector, haptic data that emulates the vital physical information isolated from the extraneous movement information of the first user;

generating, by a haptic generator, a first haptic feedback based on the selected haptic data, the first haptic feedback is unique for each type of the plurality of vital signs, the sensing device and the haptic generator being disposed in a single device that simultaneously executes sensing and haptic functions; and varying a strength of the first haptic feedback according to whether the first vital information is within a first desired zone.

22. The non-transitory computer readable storage medium of claim 21, wherein the vital physical information includes one of heart rate, blood pressure, body temperature, or body moisture.

23. The non-transitory computer readable storage medium of claim 21, further comprising instructions for identifying a physical location associated with the first user.

24. The non-transitory computer readable storage medium of claim 21, wherein the first haptic feedback emulates a characteristic of the vital physical information.

* * * * *